US009968246B2

(12) United States Patent
Iwanami (10) Patent No.: US 9,968,246 B2
(45) Date of Patent: May 15, 2018

(54) ENDOSCOPE REPROCESSOR (71) Applicant: OLYMPUS CORPORATION, Tokyo (JP)

(72) Inventor: Takayoshi Iwanami, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days. days.

(21) Appl. No.: 15/378,166

(22) Filed: Dec. 14, 2016

(65) Prior Publication Data

US 2017/0086663 A1 Mar. 30, 2017

Related U.S. Application Data (63) Continuation of application No. PCT/JP2016/059503, filed on Mar. 24, 2016.

(30) Foreign Application Priority Data

Aug. 24, 2015 (JP) .................................. 2015-164873

(51) Int. Cl.
*A61B 1/12* (2006.01)
*B08B 3/08* (2006.01)
*B08B 3/10* (2006.01)
*B08B 9/032* (2006.01)

(52) U.S. Cl.
CPC ................ *A61B 1/121* (2013.01); *B08B 3/08* (2013.01); *B08B 3/108* (2013.01); *B08B 9/032* (2013.01)

(58) Field of Classification Search
CPC ..... A61B 1/00057; A61B 1/121; A61B 1/123; A61L 2202/17; A61L 2202/24; B08B 3/08; B08B 3/108; B08B 9/032
See application file for complete search history.

(56) References Cited

U.S. PATENT DOCUMENTS

| 4,667,655 | A | * | 5/1987 | Ogiu | A61B 1/12 600/132 |
| 5,343,855 | A | * | 9/1994 | Iida | A61B 1/12 600/157 |
| 6,095,971 | A | * | 8/2000 | Takahashi | A61B 1/12 600/118 |
| 6,132,369 | A | * | 10/2000 | Takahashi | A61B 1/00068 600/159 |

(Continued)

FOREIGN PATENT DOCUMENTS

| EP | 1 767 140 A1 | 3/2007 |
| EP | 1 785 148 A2 | 5/2007 |

(Continued)

OTHER PUBLICATIONS

Extended Supplementary European Search Report dated Mar. 14, 2018 in European Patent Application No. 16 80 1944.6.

*Primary Examiner* — Marc Lorenzi
(74) *Attorney, Agent, or Firm* — Scully, Scott, Murphy & Presser, P.C.

(57) ABSTRACT

An endoscope reprocessor includes: a treatment tank configured to allow an endoscope to be disposed inside; a connector including an opening inside the treatment tank; a first conduit extending from the connector; an on-off valve disposed in the first conduit; a leak tester; and a second conduit including a conduit body having a conduit resistance that is higher than a conduit resistance of the first conduit.

4 Claims, 6 Drawing Sheets

(56) References Cited

U.S. PATENT DOCUMENTS

| | | | |
|---|---|---|---|
| 7,901,349 B2* | 3/2011 | Feld | A61B 1/00057 600/117 |
| 2005/0065405 A1* | 3/2005 | Hasegawa | A61B 1/123 600/158 |
| 2005/0196314 A1 | 9/2005 | Petersen et al. | |
| 2011/0097248 A1* | 4/2011 | Tomita | A61B 1/00059 422/292 |
| 2011/0296909 A1* | 12/2011 | Eschborn | A61B 1/00057 73/198 |

FOREIGN PATENT DOCUMENTS

| | | |
|---|---|---|
| JP | 10-243914 A | 9/1998 |
| JP | 2010-35936 A | 2/2010 |
| JP | 2010-99416 A | 5/2010 |
| JP | 2012-66018 A | 4/2012 |

* cited by examiner

ENDOSCOPE REPROCESSOR

CROSS REFERENCE TO RELATED APPLICATION

This application is a continuation application of PCT/JP2016/059503 filed on Mar. 24, 2016 and claims benefit of Japanese Application No. 2015-164873 filed in Japan on Aug. 24, 2015, the entire contents of which are incorporated herein by this reference.

BACKGROUND OF THE INVENTION

1. Field of the Invention

The present invention relates to an endoscope reprocessor.

2. Description of the Related Art

Conventionally, there have been endoscope cleaning/disinfecting apparatuses that clean/disinfect an endoscope contaminated as a result of the endoscope being used for a subject. In an endoscope cleaning/disinfecting apparatus, an endoscope is disposed in a treatment tank, an endoscope and the endoscope cleaning apparatus are connected via a tube, and air or liquid is fed into an endoscope conduit from the endoscope cleaning/disinfecting apparatus, whereby the endoscope conduit is cleaned/disinfected.

An endoscope cleaning/disinfecting apparatus includes, for example, as disclosed in Japanese Patent Application Laid-Open Publication No. 2012-66018, a check valve in an air feeding passage between a connector for tube connection, which is provided in a treatment tank, and a gas pump in order to prevent a liquid in the treatment tank from flowing into the gas pump from the connector.

SUMMARY OF THE INVENTION

An endoscope reprocessor according to an aspect of the present invention includes: a treatment tank configured to allow an endoscope to be disposed inside; a connector including an opening inside the treatment tank; a first conduit extending from the connector toward a ground side relative to the treatment tank; an on-off valve disposed in the first conduit; a leak tester including an air feeding section disposed at a position that is closer to the ground than the treatment tank; and a second conduit connecting a part of the first conduit between the on-off valve and the connector, and the leak tester, the second conduit including a conduit body having a conduit resistance that is higher than a conduit resistance of a conduit body of the first conduit.

DETAILED DESCRIPTION OF THE PREFERRED EMBODIMENT(S)

First Embodiment

Embodiments of the present invention will be described below with reference to the drawings.

Figure 1:
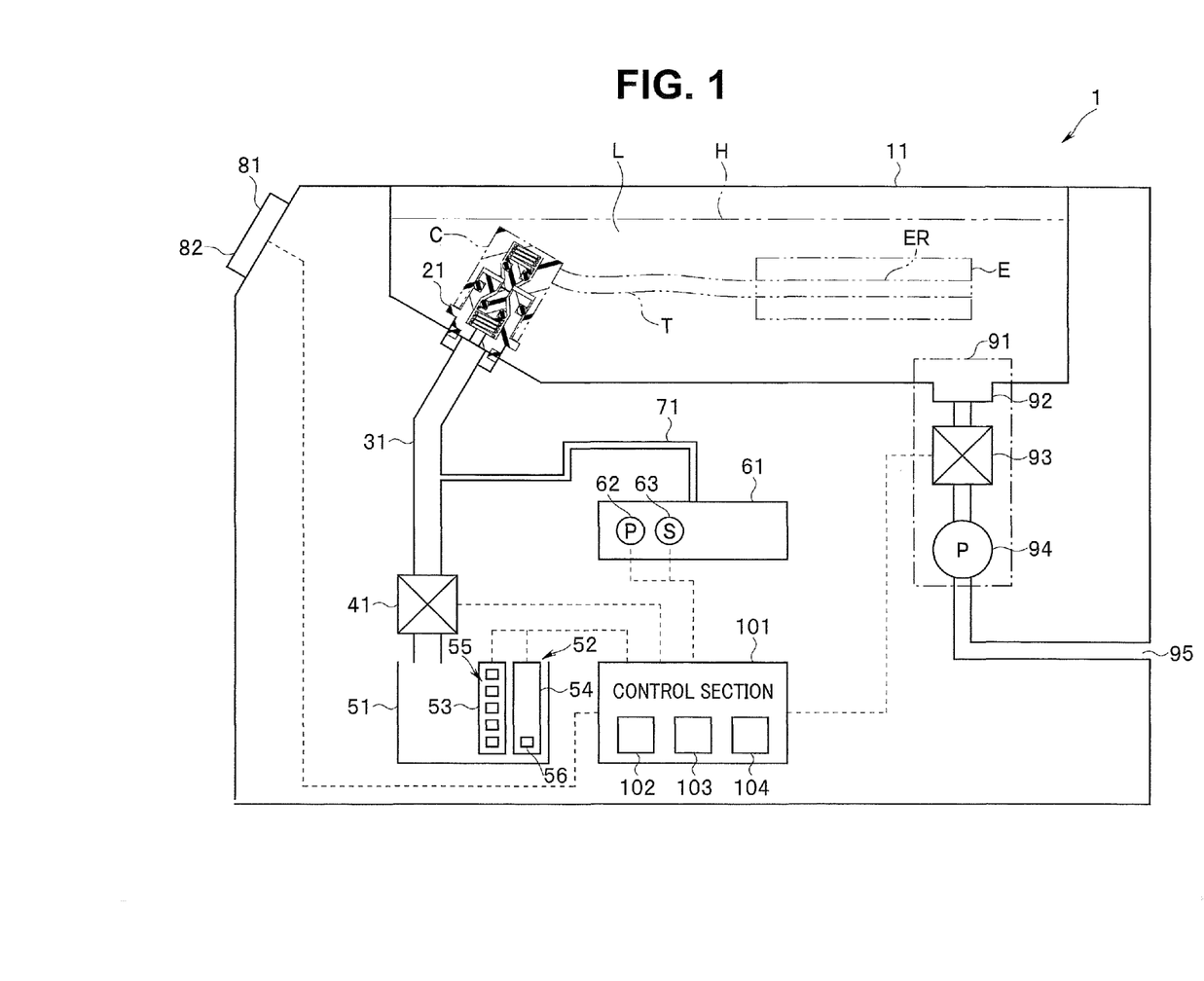
FIG. 1 is a diagram illustrating a configuration of a major part of an endoscope reprocessor according to a first embodiment of the present invention.

FIG. 1 is a diagram illustrating a configuration of a major part of an endoscope reprocessor 1 according to a first embodiment of the present invention. In FIG. 1, components other than those in the major part of the endoscope reprocessor 1 are omitted.

As illustrated in FIG. 1, the endoscope reprocessor 1 includes a treatment tank 11, a connector 21, a first conduit 31, an on-off valve 41, a water receiving section 51, a leak tester 61, a second conduit 71, a notification section 81, a liquid discharge section 91 and a control section 101. An endoscope E is connected to the connector 21. The connector 21 and the endoscope E may be connected directly or a tube T may be interposed therebetween.

As illustrated in FIG. 1, the treatment tank 11 is formed in a recessed shape so that the endoscope E can be disposed and a liquid L such as water, a cleaning liquid, a disinfectant liquid, a sterile liquid or alcohol can be stored. The treatment tank 11 is connected to a liquid discharge section 91 configured to discharge the liquid L stored in the treatment tank 11. The treatment tank 11 includes the connector 21 for connecting the endoscope E. The treatment tank 11 can store the liquid L up to a water level H located at a position that is further away from the ground than the connector 21. When the liquid L is stored up to the water level H in the treatment tank 11, the connector 21 is submerged in the liquid L in the treatment tank 11.

The endoscope reprocessor 1 can perform reprocessing of the endoscope E with the connector 21 submerged. Along with reprocessing of the endoscope E, the connector 21 comes into contact with the liquid L in the treatment tank 11.

Figure 2:
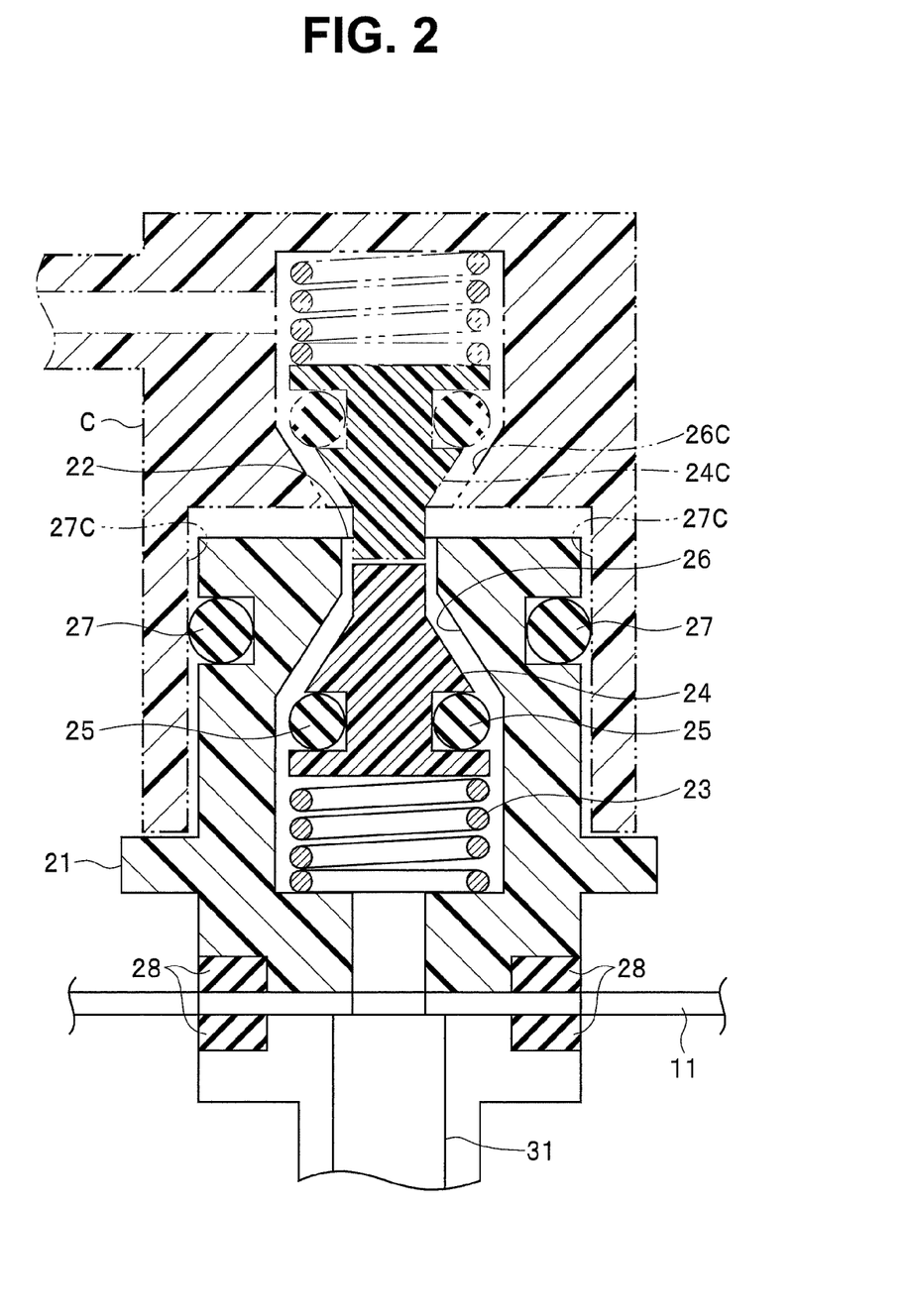
FIG. 2 is a cross-sectional diagram illustrating a configuration of a connector in the endoscope reprocessor according to the first embodiment of the present invention.

FIG. 2 is a cross-sectional diagram illustrating a configuration of the connector 21 in the endoscope reprocessor 1 according to the first embodiment of the present invention. FIG. 2 indicates a state in which a tube connector C is attached to the connector 21. In FIG. 2, the connector 21 is indicated by solid lines, and the tube connector C attached to the connector 21 is indicated by alternate long and two short dashes lines.

The connector 21 includes an opening 22 inside the treatment tank 11. The connector 21 is configured in such a manner that, in a state in which the tube connector C is removed, a coil spring 23, which is a pressure spring, supports a valve disc 24 by means of an elastic force and an O-shaped ring 25 provided on the valve disc 24 is pressed against an inner wall 26 of the connector, thereby preventing the liquid L stored in the treatment tank 11 from flowing into the first conduit 31 via the opening 22.

Upon attachment of the tube connector C to the connector 21, a distal end of the valve disc 24 of the connector 21 and a distal end of a valve disc 24C of the tube connector C are pressed against each other, the valve disc 24C pushes the valve disc 24 in against the elastic force of the coil spring 23, and a gap is formed between the valve disc 24 and the inner wall 26 of the connector, and a gap is also formed between valve disc 24C and an inner wall 26C of the tube connector, respectively, whereby the connector 21 and the tube connector C communicate with each other.

Upon attachment of the tube connector C to the connector 21, an O-shaped ring 27 provided on an outer periphery of the connector 21 is pressed against an inner wall 27C of the tube connector, whereby the liquid L stored in the treatment tank 11 is prevented from flowing into the opening 22 from the gap between the valve disc 24 and the inner wall 26 of the connector.

In order to prevent the liquid L in the treatment tank 11 from flowing into the first conduit 31 via a part to which the connector 21 is attached, packing 28 is provided in a part of the connector 21, the part being adjacent to the treatment tank 11.

The connector 21 is connected to the first conduit 31.

Each of the O-shaped ring 25, the O-shaped ring 27 and the packing 28 includes, for example, a material that can keep water-tightness such as rubber or a synthetic resin.

If the O-shaped ring 25, the O-shaped ring 27 or the packing 28 fails to keep water-tightness because of deterioration or damage as a result of repetition of attachment/detachment of the tube connector C to/from the connector 21, the liquid L stored in the treatment tank 11 flows into the first conduit 31.

Figure 3:
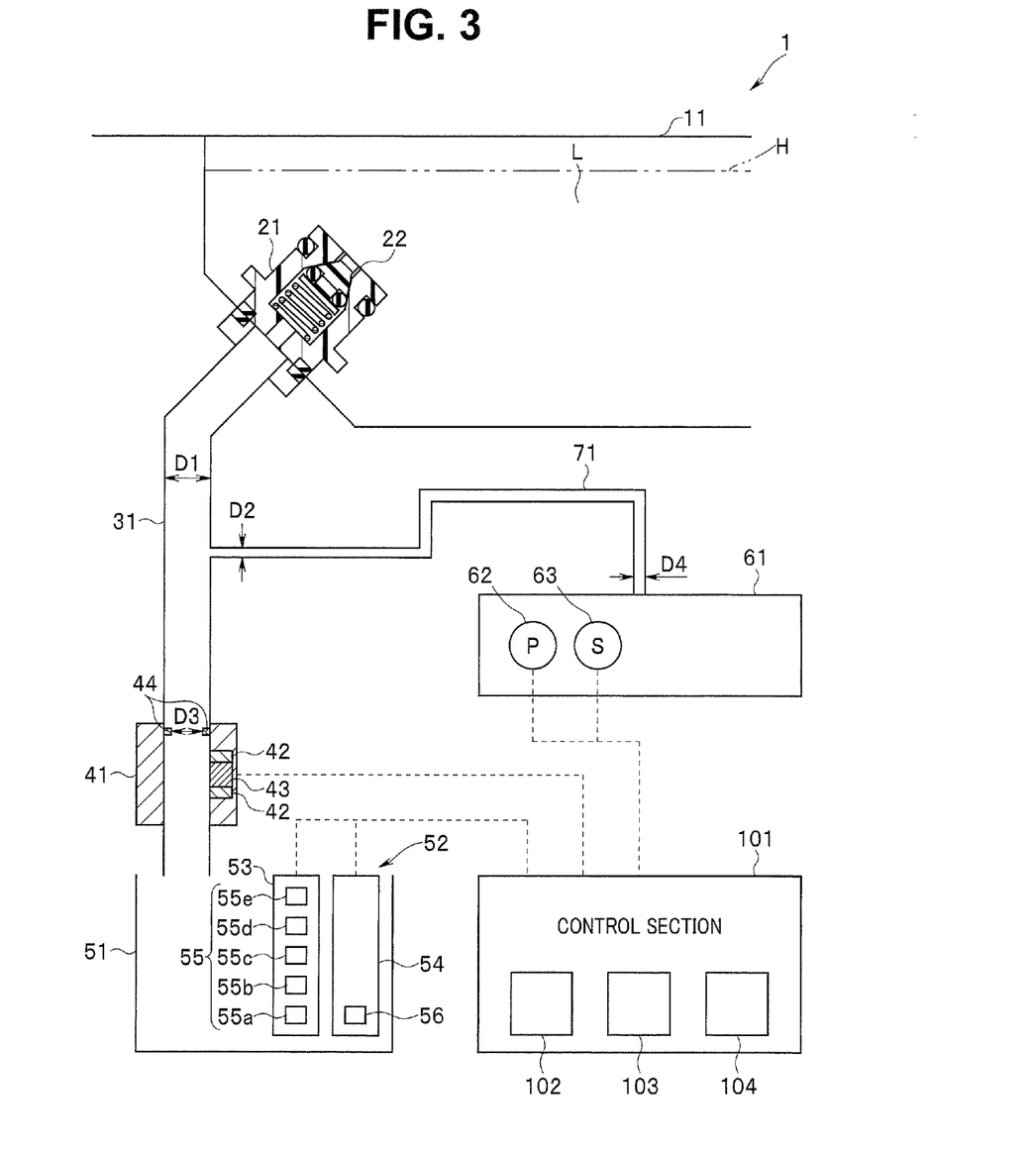
FIG. 3 is a diagram illustrating a configuration of a major part of the endoscope reprocessor according to the first embodiment of the present invention.

FIG. 3 is a diagram illustrating a configuration of a major part of the endoscope reprocessor 1 according to the first embodiment of the present invention. In FIG. 3, components other than those in the major part of the endoscope reprocessor 1 are omitted.

The first conduit 31 includes a round tube having a round shape in cross section. As illustrated in FIG. 3, one end portion of the first conduit 31 is connected to the connector 21 of the treatment tank 11, the first conduit 31 extends obliquely downward from the connector 21 and successively extends vertically downward, and the other end portion of the first conduit 31 is successively connected to a water receiving section 51 located below the treatment tank 11. In other words, the first conduit 31 extends from the connector 21 toward the ground side relative to the treatment tank 11. Directions of the extension to the ground side include the obliquely downward direction and the vertically downward direction.

The second conduit 71 is connected to an intermediate portion of the first conduit 31. The first conduit 31 includes the on-off valve 41 in a lower portion thereof.

A conduit body of the second conduit 71 is configured so as to have a conduit resistance that is higher than that of the conduit body of the first conduit 31. A conduit resistance of a conduit body here refers to a resistance caused by a shape and properties the conduit itself has such as a cross-sectional area, a bending shape and/or a material of the conduit, the resistance not including a resistance caused by a check valve when the check valve is provided in the conduit.

A flow passage cross-sectional area of the first conduit 31 is larger than a flow passage cross-sectional area of the second conduit 71. In other words, a conduit diameter D1 of the first conduit 31 is larger than a conduit diameter D2 of the second conduit 71. As a result, the conduit resistance of the conduit body of the second conduit 71 is higher than that of the first conduit 31.

The on-off valve 41 includes an electromagnetic valve. The on-off valve 41 includes a solenoid 42, a valve disc 43 and an orifice 44.

The solenoid 42 is electrically connected to the control section 101. The solenoid 42 can generate a magnetic field to actuate the valve disc 43, in response to a control signal from the control section 101.

The valve disc 43 is actuated by the magnetic field generated by the solenoid 42 and can open/close the on-off valve 41.

The orifice 44 has an orifice diameter D3 that is smaller than the conduit diameter D1 of the first conduit 31, and can adjust a flow rate in the on-off valve 41.

The on-off valve 41 is normally in an opened state. In a leak test, which will be described later, upon the solenoid 42 receiving a control signal from the control section 101, the solenoid 42 actuates the valve disc 43 to bring the on-off valve 41 into a closed state.

The water receiving section 51 includes a receiving pan, an upper portion of which is opened. The water receiving section 51 can receive and store the liquid L such as water discharged from the first conduit 31. In the water receiving section 51, a water level sensor 52 is disposed.

The water level sensor 52 is, for example, an electrode-type water level sensor 52, and includes two electrode bars 53, 54. In one electrode bar 53, water level electrodes 55 are disposed at respective water levels to be detected. Although a plurality of water level electrodes 55 are arranged vertically in the figure, the present invention is not limited to this case and a single water level electrode 55 may be provided. In the other electrode bar 54, a ground electrode 56 is disposed. The water level sensor 52 is electrically connected to the control section 101.

Note that, although as the water level electrodes 55, five water level electrodes 55a, 55b, 55c, 55d, 55e are indicated in FIG. 3, the number of water level electrodes 55 is not limited to five. Also, in the below, any one of the water level electrodes or the five water level electrodes are referred to as water level electrode(s) 55.

When the liquid L discharged from the first conduit 31 is stored in the water receiving section 51, a water level electrode 55 corresponding to a water level and the ground electrode 56 are made to be electrically continuous with each other, and the water level sensor 52 outputs information on the water level to the control section 101.

The leak tester 61 can detect whether or not air leaks from the inside of the endoscope E. If air leaks from the endoscope E, there is possibly a hole in an outer casing of the endoscope E or an endoscope conduit ER. The leak tester 61 is disposed at a position that is closer to the ground than the treatment tank 11. A connection port diameter D4 of the leak tester 61 or a non-illustrated diameter of a conduit inside the leak tester 61 is set to be smaller than the orifice diameter D3. The leak tester 61 includes a gas pump 62, which is an air feeding section, and a pressure sensor 63.

The gas pump 62, which is an air feeding section, can pressurize and feed air. The gas pump 62 is opened to atmosphere via a non-illustrated conduit opened to the atmosphere. The gas pump 62 is electrically connected to the control section 101. Upon receipt of a control signal from the control section 101, the gas pump 62 takes air in from the atmosphere and can pressurize the inside of the endoscope E via the tube T.

The pressure sensor 63 can measure a pressure inside the endoscope E. The pressure sensor 63 is electrically connected to the control section 101. The pressure sensor 63 can measure the pressure inside the endoscope E and output information on a result of the measurement to the control section 101.

The leak tester 61 is connected to the endoscope E via the tube T, and can pressurize the inside of the endoscope E by means of the gas pump 62, measure the pressure inside the endoscope E by means of the pressure sensor 63, and output a result of the measurement to the control section 101.

Although a cross-sectional structure of the second conduit 71 is not specifically limited, the second conduit 71 includes, for example, a round tube having a round shape in cross section. The second conduit 71 is configured so as to connect a part of the first conduit 31 between the on-off valve 41 and the connector 21, and the leak tester 61.

The conduit diameter D2 of the second conduit 71 is made to be smaller than the conduit diameter D1 of the first conduit 31 so that the conduit body of the second conduit 71 has a conduit resistance that is higher than that of the conduit body of the first conduit 31.

In the second conduit 71, an inner portion of the conduit includes a flexed portion flexed in a direction away from the ground. A surface of the conduit may be bent as with the inner portion of the conduit, and only the inner portion of the conduit may be bent while the surface of the conduit is straight.

The flexed portion may be one formed by connecting straight tunnels such as in FIG. 4 or may be a curved tunnel such as described later.

Referring back to FIG. 1, the notification section 81 includes a display section 82. The notification section 81 is connected to the control section 101. Upon receipt of a control signal for providing an error indication from the control section 101, the notification section 81 makes the display section 82 provide an error indication.

The liquid discharge section 91 includes a water discharge port 92, a water discharge valve 93, a water discharge pump 94, and an external discharge port 95.

The water discharge port 92 enables discharge of the liquid L stored in the treatment tank 11.

The water discharge valve 93 includes an electromagnetic valve. The water discharge valve 93 is electrically connected to the control section 101. The water discharge valve 93 receives a control signal from the control section 101, and when the liquid L is stored in the treatment tank 11, the water discharge valve 93 is brought into a closed state, and when the liquid L is discharged from the treatment tank 11, the water discharge valve 93 is brought into an opened state.

The water discharge pump 94 includes a liquid pump, and can take in the liquid L from the treatment tank 11 and pressurize and discharge the liquid for quicker discharge of the liquid L from the treatment tank 11.

The external discharge port 95 is connected to non-illustrated external water discharge means and allows discharge of the liquid L from the treatment tank 11 to the external water discharge means.

The control section 101 includes a central processing unit (hereinafter referred to as "CPU") 102, a ROM 103 and a RAM 104. The CPU 102 can read various processing programs relating to liquid leak detection, which are recorded in the ROM 103, and develop the programs on the RAM 104 and execute the programs. Functions of the CPU 102 are provided by execution of various processing programs recorded in the ROM 103.

The control section 101 is connected to the on-off valve 41, the water level sensor 52, the leak tester 61, the notification section 81 and the liquid discharge section 91.

If the water level sensor 52 detects that a water level in the water receiving section 51 exceeds a predetermined water level, the control section 101 transmits a control signal for providing an error indication to the display section 82 to make the display section 82 provide an error indication.

The predetermined water level is set in advance to a water level at which a liquid leak from the connector can be detected.

If the water level sensor 52 detects that a water level in the water receiving section 51 exceeds the predetermined water level, the control section 101 transmits a control signal for bringing the water discharge valve 93 into an opened state to the water discharge valve 93 to bring the water discharge valve 93 into an opened state, and transmits a control signal for driving the water discharge pump 94 to the water discharge pump 94 to drive the liquid discharge section 91, whereby the liquid L in the treatment tank 11 is discharged to the external water discharge means.

Operation

Next, liquid leak detection processing in the endoscope reprocessor 1 according to the first embodiment will be described.

Upon provision of an instruction to start processing such as cleaning/disinfecting of the endoscope reprocessor 1 by a user via a non-illustrated operation section, the CPU 102 reads the liquid leak detection programs in addition to programs for processing such as cleaning/disinfecting, and develops the programs in the RAM 104 and start performing the processing.

The control section 101 supplies a liquid L such as water, a cleaning liquid, a disinfectant liquid, a sterile liquid or alcohol to the treatment tank 11 from a non-illustrated nozzle to store the liquid L up to a water level H in the treatment tank 11. When the liquid L is stored up to the water level H, the connector 21 is submerged in the liquid L.

If there is a liquid leak from the connector 21 due to deterioration or damage of the connector 21, the O-shaped ring 25, the O-shaped ring 27 or the packing 28, the liquid L in the treatment tank 11 flows through the first conduit 31 having a conduit resistance that is smaller than that of the second conduit 71 and is stored in the water receiving section 51.

When the liquid L is stored in the water receiving section 51, the water level sensor 52 detects a water level and outputs information on the water level to the control section 101.

If the water level in the water receiving section 51 exceeds a predetermined water level, the control section 101 transmits a control signal to each of the display section 82, a water discharge valve 93 and a water discharge pump 94 to make the display section 82 provide an error indication, bring the water discharge valve 93 into an opened state, and drive the water discharge pump 94 to discharge the liquid L from the treatment tank 11.

After the discharge of the liquid L from the treatment tank 11, the user can, e.g., inspect, repair or replace the connector 21.

As described above, the conduit resistance of the second conduit 71 is set to be larger than that of the first conduit 31. In other words, the conduit diameter D2 of the second conduit 71 is set to be smaller than the conduit diameter D1 of the first conduit 31 so that the conduit resistance of the second conduit 71 is larger than that of the first conduit 31. The connection port diameter D4 of the leak tester 61 or the non-illustrated diameter of the conduit in the leak tester 61 is set to be smaller than the orifice diameter D3 so that the conduit resistance of the second conduit 71 is larger than that of the first conduit 31.

Consequently, in the endoscope reprocessor 1, even if there is a liquid leak from the connector 21, the liquid L in the treatment tank 11 flows through the first conduit 31 having a conduit resistance that is smaller than that of the second conduit 71, enabling the liquid L in the treatment tank 11 to be prevented from flowing into the gas pump 62.

Next, leak test processing in the endoscope reprocessor 1 according to the first embodiment will be described.

Upon a user connecting the endoscope E to the connector 21 via the tube T and providing an instruction to start a leak test via the non-illustrated operation section, the control section 101 transmits a control signal for bringing a valve into a closed state, to the on-off valve 41 to bring the on-off valve 41 into a closed state. Upon the on-off valve 41 being brought into a closed state, the control section 101 transmits a control signal for driving the gas pump 62 to the gas pump 62 and thereby drives the gas pump 62 to pressurize the inside of the endoscope E. After the pressurization of the inside of the endoscope E, the pressure sensor 63 measures a pressure inside the endoscope E, and outputs information on a result of the measurement to the control section 101. If the pressure inside the endoscope E is higher than a predetermined pressure, the control section 101 determines there is no air leak from the endoscope E. On the other hand, if the pressure inside the endoscope E is lower than the predetermined pressure, the control section 101 determines that there is an air leak from the endoscope E. The control section 101 makes the display section 82 indicate the result of the determination.

Consequently, since each of the first conduit 31 and the second conduit 71 has no check valve, the gas pump 62 can feed air with no pressure loss caused by a check valve, and thus, the pressure sensor 63 can more correctly measure the pressure inside the endoscope E.

The above-described first embodiment enables provision of an endoscope reprocessor 1 that can prevent a liquid L in a treatment tank 11 from flowing into a gas pump 62 and more correctly measure a pressure inside an endoscope E in a leak test.

Second Embodiment

Although in the first embodiment, the first conduit 31 includes no chamber 32, a first conduit 31a may include a chamber 32.

Next, a second embodiment in which a first conduit 31a includes a chamber 32 will be described. Note that, in the description of the second embodiment, description of components that are the same as those of the first embodiment will be omitted.

Figure 4:
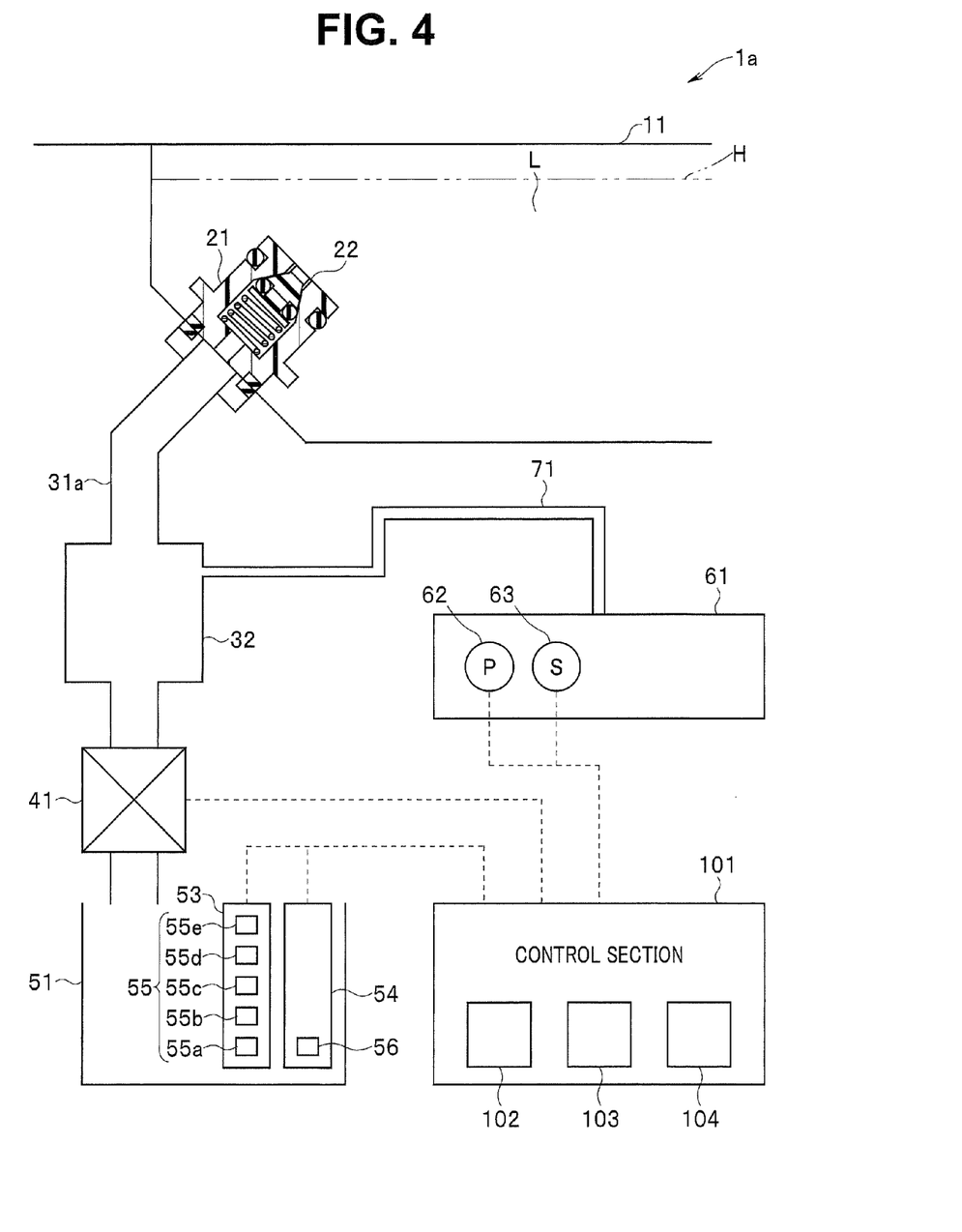
FIG. 4 is a diagram illustrating a configuration of a major part of an endoscope reprocessor according to a second embodiment of the present invention.

FIG. 4 is a diagram illustrating a configuration of a major part of an endoscope reprocessor 1a according to the second embodiment of the present invention. In FIG. 4, components other than those in the major part of the endoscope reprocessor 1a are omitted.

A first conduit 31a in the endoscope reprocessor 1a includes a chamber 32 in an intermediate portion.

The chamber 32 includes, for example, a round cylinder or a rectangular cylinder including a hollow inner portion. A flow passage cross-sectional area of the chamber 32 is set to be larger than respective flow passage cross-sectional areas of the first conduit 31a and a second conduit 71. The second conduit 71 is connected to the chamber 32.

With this configuration, a conduit resistance of the second conduit 71 is set to be larger than that of the chamber 32. Consequently, even if there is a liquid leak from the connector 21, a liquid L in a treatment tank 11 flows through the first conduit 31a having a conduit resistance that is smaller than that of the second conduit 71, enabling the liquid L in the treatment tank 11 to be prevented from flowing into the gas pump 62.

Third Embodiment

Although in the first embodiment and the second embodiment, the second conduit 71 is configured in such a manner that an inner portion of the conduit includes a flexed portion flexed in a direction away from the ground, the second conduit 71 may be configured in such a manner that the inner portion of the conduit includes at least one bent portion 72 bent so as to project in the direction away from the ground.

Figure 5:
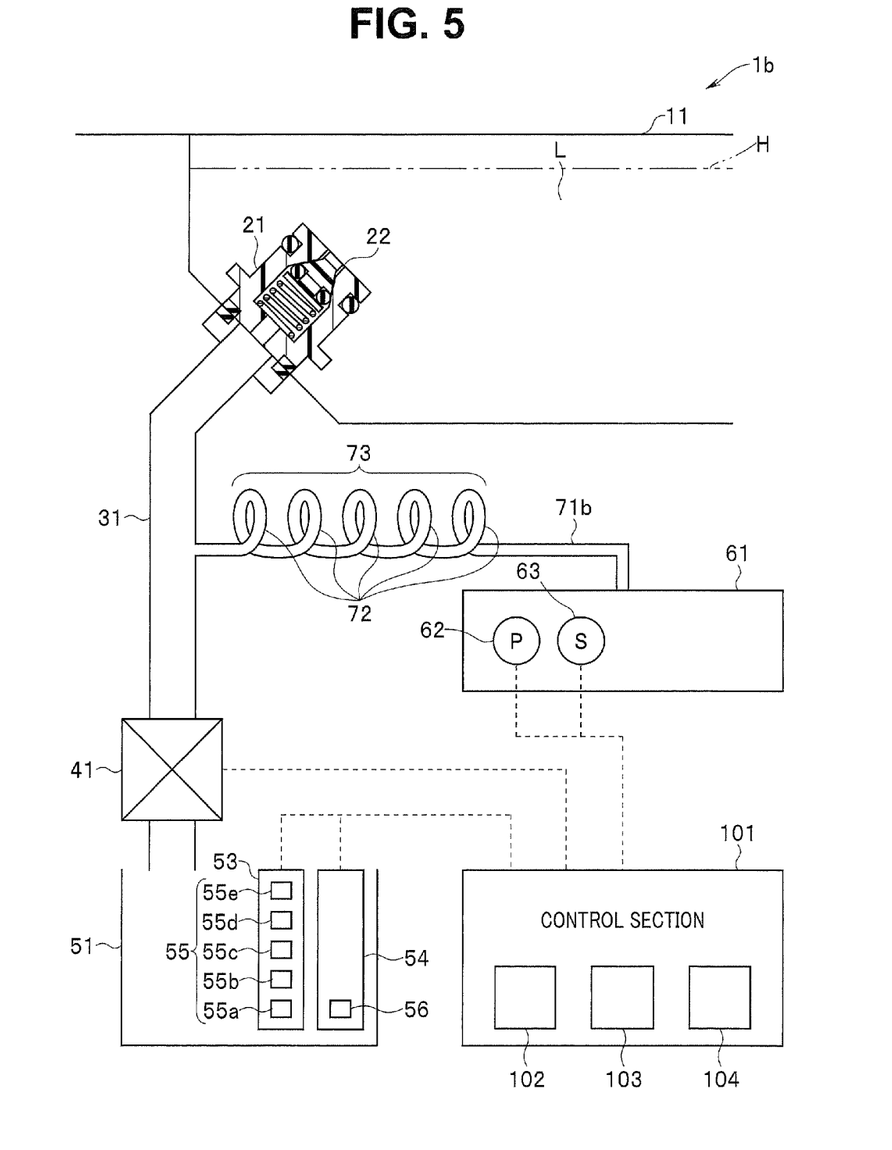
FIG. 5 is a diagram illustrating a configuration of a major part of an endoscope reprocessor according to a third embodiment of the present invention.

FIG. 5 is a diagram illustrating a configuration of a major part of an endoscope reprocessor 1b according to a third embodiment of the present invention. In FIG. 5, components other than those in the major part of the endoscope reprocessor 1b are omitted.

A second conduit 71b of the endoscope reprocessor 1b is configured in such a manner that an inner portion of the conduit includes a plurality of bent portions 72 bending so as to project in a direction away from a ground. More specifically, in the second conduit 71b, a helix 73 is formed by the plurality of bent portions 72 that are continuous with one another (in the example in FIG. 5, a 5-turn helix 73 is formed). The second conduit 71b has a conduit length that is larger than a conduit length of the first conduit 31.

With this configuration, the second conduit 71b has a conduit length that is larger than that of the first conduit 31 and includes at least one bent portion 72 projecting in a direction away from a ground, and thus, the second conduit 71b has a conduit resistance that is larger than that of the first conduit 31. Consequently, even if there is a liquid leak from the connector 21, a liquid L in a treatment tank 11 flows through the first conduit 31 having a conduit resistance that is smaller than that of the second conduit 71b, enabling the liquid L in the treatment tank 11 to be prevented from flowing into a gas pump 62.

Fourth Embodiment

Although in the first embodiment, the second embodiment and the third embodiment, the second conduit 71 or 71b is disposed at a position that is closer to the ground than the treatment tank 11, a second conduit 71c may include a part raised to a position that is further away from a ground than a water level H in a treatment tank 11.

Also, although in the first embodiment, the second embodiment and the third embodiment, the first conduit 31 or 31a is connected to the water receiving section 51 including the water level sensor 52, the first conduit 31 or 31a may be connected to a liquid sensor 57 configured to detect contact with a liquid L.

Figure 6:
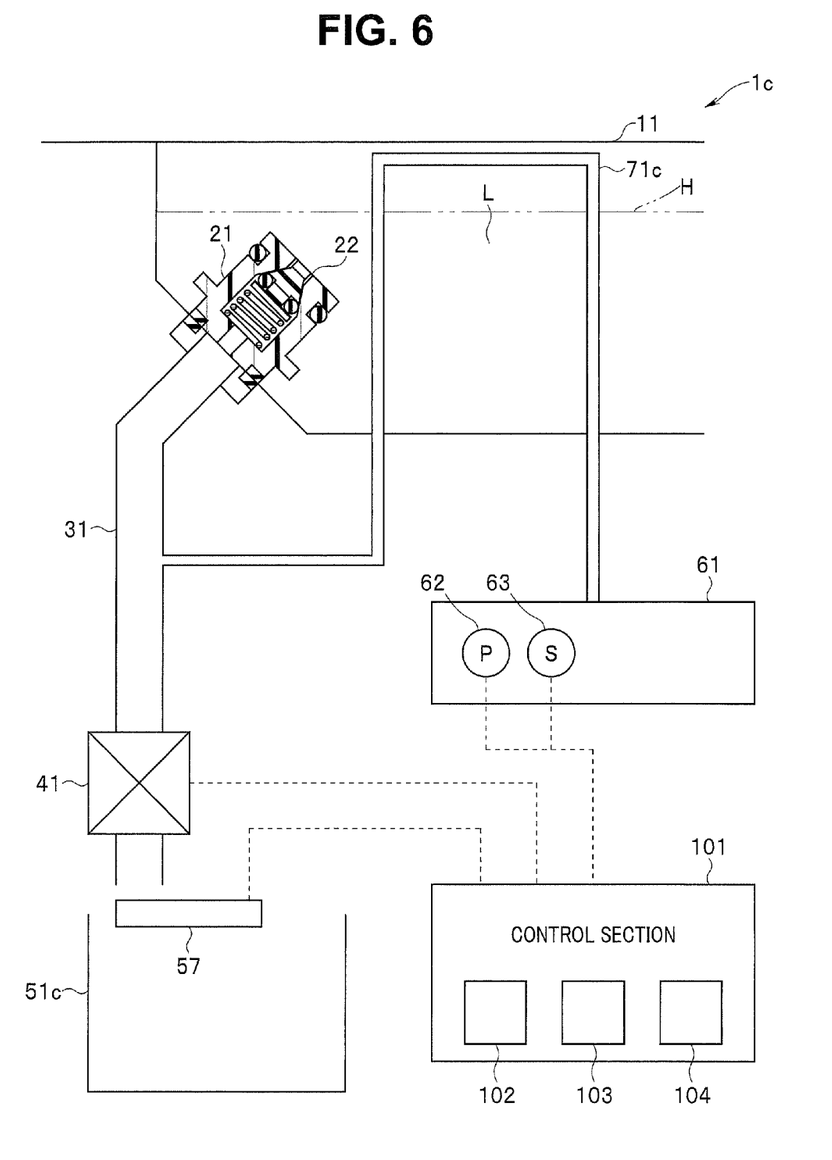
FIG. 6 is a diagram illustrating a configuration of a major part of an endoscope reprocessor according to a fourth embodiment of the present invention.

FIG. 6 is a diagram illustrating a configuration of a major part of an endoscope reprocessor 1c according to a fourth embodiment of the present invention. In FIG. 6, components other than those in the major part of the endoscope reprocessor 1c are omitted.

A second conduit 71c in the endoscope reprocessor 1c is configured so as to be connected to an intermediate portion of a first conduit 31 and be connected to a leak tester 61 through an upper edge 12 of a treatment tank 11, the upper edge 12 being located at a position that is further away from a ground than a water level H of a liquid L stored in the treatment tank 11.

With this configuration, since a part of the second conduit 71c extends through the position that is further away from the ground than the water level H, a conduit resistance of the second conduit 71c is set to be larger than that of the first conduit 31. Consequently, even if there is a liquid leak from the connector 21, the liquid L in the treatment tank 11 flows through the first conduit 31 having a conduit resistance that is smaller than that of the second conduit 71, enabling the liquid L in the treatment tank 11 to be prevented from flowing into the gas pump 62.

A water receiving section 51c includes a liquid sensor 57 connected to the first conduit 31. The liquid sensor 57 is connected to a control section. Upon the liquid L discharged from the first conduit 31 coming into contact with the liquid sensor 57, the liquid sensor 57 detects the liquid L and outputs information indicating the detection of the liquid to the control section 101.

With this configuration, the liquid L discharged from the first conduit 31 can promptly be detected before the liquid L is stored in the water receiving section 51c.

The first embodiment, the second embodiment, the third embodiment and the fourth embodiment (hereinafter referred to as the "first embodiment and the like") each enable provision of an endoscope reprocessor 1 that can prevent a liquid L in a treatment tank 11 from flowing into a gas pump 62 and more correctly measure a pressure inside an endoscope E in a leak test.

Note that, although in the first embodiment and the like, the first conduit 31 or 31a and the second conduit 71, 71b or 71c each include a round tube having a round shape in cross section, the first conduit 31 or 31a and the second conduit 71, 71b or 71c are not necessarily required to include a round tube having a round shape in cross section. The first conduit 31 or 31a and the second conduit 71, 71b or 71c may each have, for example, an elliptical shape, an elongated round shape, a rectangular shape or a triangular shape in cross section.

Note that, although in the first embodiment and the like, the water receiving section 51 is included, a configuration in which no water receiving section 51 is included, an end portion of the first conduit 31 or 31a is connected to the external discharge port 95 to directly discharge the liquid L flowing into the first conduit 31 or 31a to the outside may be employed.

Note that, although in the first embodiment and the like, the water receiving section 51 includes a receiving pan, an upper portion of which is opened, the water receiving section 51 may have any shape as long as the shape allows storage of a liquid L such as water. The water receiving section 51 may include, for example, a tank, a bottle or a box.

Note that, although in the first embodiment and the like, the water level sensor 52 includes an electrode-type water level sensor 52, a water level sensor may include what is called a float-type water level sensor configured to detect a water level via a float.

Note that, although in the first embodiment and the like, in the second conduit 71, 71b or 71c, the inner portion of the conduit includes a flexed portion flexed so as to project in the direction away from the ground, the second conduit is not necessarily required to include a flexed portion. In such case, if the second conduit 71 is inclined away from the ground from the first conduit 31 side toward the leak tester 61 side, the conduit resistance of the second conduit 71 becomes larger than that of the first conduit 31.

Note that, although in the first embodiment and the like, the notification section 81 includes the display section 82, the notification section 81 may include a sound generating section in order to notify a user of an error by means of a sound.

Note that the endoscope reprocessor 1 is an apparatus that performs reprocessing of contaminated endoscope E or endoscope accessories. Reprocessing mentioned here is not specifically limited, and may be water rinsing, cleaning for removing dirt of, e.g., organic substances, disinfection for making predetermined microorganisms harmless and sterilization for eliminating or killing all microorganisms or any combination thereof.

The present invention is not limited to the above-described embodiments, and various modifications, alterations and the like are possible without departing from the spirit of the present invention.

The present invention enables provision of an endoscope reprocessor that can prevent a liquid in a treatment tank from flowing into a gas pump and more correctly measure a pressure inside an endoscope in a leak test.

What is claimed is:

1. An endoscope reprocessor comprising:
    a treatment tank configured to allow an endoscope to be disposed inside;
    a connector including an opening inside the treatment tank;
    a first conduit extending from the connector toward a ground side relative to the treatment tank;
    an on-off valve disposed in the first conduit;
    a leak tester including a gas pump and a pressure sensor, the gas pump being configured to supply gas to the endoscope through the connector, the leak tester being disposed at a position that is closer to the ground than the treatment tank, and the leak tester being configured to test a leak of the gas in the endoscope;
    a first conduit opening provided at a position on the first conduit between the on-off valve and the connector; and
    a second conduit connecting the first conduit opening and the leak tester to each other, the second conduit including a conduit body having a conduit resistance that is higher than a conduit resistance of a conduit body of the first conduit, and the second conduit being directly connected to the first conduit opening and the leak tester.

2. The endoscope reprocessor according to claim 1, wherein the first conduit has a flow passage cross-sectional area that is larger than a flow passage cross-sectional area of the second conduit.

3. The endoscope reprocessor according to claim 2, wherein the first conduit has a conduit diameter that is larger than a conduit diameter of the second conduit.

4. The endoscope reprocessor according to claim 1, wherein in the second conduit, an inner portion of the second conduit includes at least one flexed portion flexed in a direction away from the ground.

* * * * *